(12) United States Patent
Shen et al.

(10) Patent No.: US 7,445,857 B2
(45) Date of Patent: Nov. 4, 2008

(54) ORGANOMETALLIC COMPLEX AND ORGANIC ELECTROLUMINESCENT DEVICES UTILIZING THE SAME

(75) Inventors: Kuo-Hui Shen, Kaohsiung County (TW); Shu-Tang Yeh, Taichung County (TW); Heh-Lung Huang, Taipei County (TW); I-Ho Shen, Yunlin County (TW); Miao-Tsai Chu, Taipei County (TW); Tien-Shou Shieh, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 521 days.

(21) Appl. No.: 11/212,796

(22) Filed: Aug. 29, 2005

(65) Prior Publication Data

US 2007/0237981 A1 Oct. 11, 2007

(30) Foreign Application Priority Data

Dec. 22, 2004 (TW) .............................. 93140061 A (51) Int. Cl.
*H01L 51/54* (2006.01)
*C09K 11/06* (2006.01)

(52) U.S. Cl. .................. 428/690; 428/917; 313/504; 313/506; 257/40; 257/E51.044; 546/4; 546/10; 549/3

(58) Field of Classification Search .............. 546/4, 546/10; 549/3; 428/690, 917; 313/504, 313/506; 257/40, E51.044
See application file for complete search history.

(56) References Cited

U.S. PATENT DOCUMENTS

| | | | |
|---|---|---|---|
| 2002/0024293 A1 | 2/2002 | Igarashi et al. | |
| 2002/0034656 A1 | 3/2002 | Thompson et al. | |
| 2002/0045061 A1 | 4/2002 | Hosokawa | |
| 2003/0017361 A1 | 1/2003 | Thompson et al. | |
| 2003/0068526 A1* | 4/2003 | Kamatani et al. ........... | 428/690 |
| 2003/0072964 A1* | 4/2003 | Kwong et al. .............. | 428/690 |
| 2003/0092935 A1 | 5/2003 | Ahlers | |
| 2003/0102800 A1 | 6/2003 | Kuo et al. | |
| 2004/0053071 A1 | 3/2004 | Igarashi et al. | |
| 2004/0086743 A1 | 5/2004 | Brown et al. | |
| 2004/0102632 A1 | 5/2004 | Thompson et al. | |
| 2004/0110031 A1 | 6/2004 | Fukuda et al. | |

FOREIGN PATENT DOCUMENTS

| | | |
|---|---|---|
| EP | 1 434 286 A1 | 6/2004 |
| JP | 2002-226495 A | 8/2002 |
| JP | 2002-338588 A | 11/2002 |
| JP | 2003-109758 A | 4/2003 |
| JP | 2003-113246 A | 4/2003 |
| JP | 2003-119179 A | 4/2003 |
| JP | 2003-123982 A | 4/2003 |
| JP | 2003-147021 A | 5/2003 |
| JP | 2003-171391 A | 6/2003 |
| JP | 2003-206320 A | 7/2003 |
| JP | 2003-253128 A | 9/2003 |
| JP | 2003-253129 A | 9/2003 |
| JP | 2003-253145 A | 9/2003 |
| JP | 2004-111379 A | 4/2004 |
| WO | WO-03/040250 A1 | 5/2003 |
| WO | WO-2004/026886 A2 | 4/2004 |
| WO | WO-2004/028217 A1 | 4/2004 |
| WO | WO-2004/037836 A1 | 5/2004 |
| WO | WO-2004/048395 A1 | 6/2004 |
| WO | WO-2004/055130 A1 | 7/2004 |

OTHER PUBLICATIONS

Baldo et al., Nature, vol. 395, Sep. 10, 1998, pp. 151-154.
Lamansky et al., J. Am. Chem. Soc. 2001, vol. 123, No. 18, pp. 4304-4312.
Tamayo et al., J. Am. Chem. Soc. 2003, vol. 125, No. 24, pp. 7377-7387.

* cited by examiner

*Primary Examiner*—Callie E Shosho
*Assistant Examiner*—Michael Wilson
(74) *Attorney, Agent, or Firm*—Birch, Stewart, Kolasch & Birch, LLP (57) ABSTRACT

An organometallic complex. The organometallic complex has formula (I):

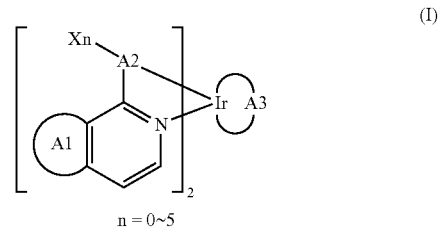

n = 0~5 wherein A1 is a substituted or non-substituted aromatic heterocyclic group, A2 is a substituted or non-substituted aryl group, A3 is an acetylacetone group or picolinic acid group, and X is selected from the group consisting of fluorine atom, trifluoromethyl, alkoxy, thioalkyl, and amino. The invention also provides an organic electroluminescent device utilizing the organometallic complex.

15 Claims, 1 Drawing Sheet

FIG. 1

ORGANOMETALLIC COMPLEX AND ORGANIC ELECTROLUMINESCENT DEVICES UTILIZING THE SAME

BACKGROUND

The present invention relates to an organometallic complex, and more specifically to an organometallic complex used in an organic electroluminescent device.

Organic electroluminescent diode research began with Pope in 1962, providing single crystal luminescent naphthalene under application of an external voltage. A double-layer organic thin film device was then provided by Tan (Kodak Corporation) in 1982, significantly increasing brightness and luminescent efficiency and leading to follow-up research. Applications regarding organometallic complexes used in organic electroluminescent devices began in 1980, such as Pt(II), Ru(II), Os(II), Eu(III), and Ir(III) complexes, of which Ir(III) complexes were the most popular.

Initial doped red phosphorescent complexes were provided by M. E. Thompson and S. R. Forest as disclosed in Nature, 395, 1988, pages 151~154, providing Pt as a metal center of a complex with a luminescent wavelength of 650 nm, quantum efficiency of 1.3%, and luminescent intensity of 0.15 lm/W under a current density of 100 cd/A. More types of Ir complexes were provided by M. E. Thompson in 2001 (J. Am. Chem. Soc. 2001, 123, 4304~4312), with luminescent wavelengths across red, green, and blue light regions. In 2003, M. E. Thompson further provided a comparison of luminescent efficiency and lifetime between facial and meridional isomers of a Ir complex as disclosed in J. Am. Chem. Soc. 2003, 125, 7377~7387. Other related technology is disclosed in U.S. Pre-Grant Pat. No. 2002024293, 2002034656, 2002045061, 2003017361, 2003092935, 2003102800, 2004053071, 2004102632, 2004086743, and 2004110031, in J. P. Pre-Grant Pat. No. 2002226495, 2002338588, 2003109758, 2003113246, 2003119179, 2003123982, 2003147021, 2003171391, 2003206320, 2003253128, 2003253129, 2003253145, and 2004111379, and in G. P Pre-Grant Pat. No. 2004026886, 2004028217, 2004037836, 2004048395, and 2004055130.

Various Ir complexes have been provided, such as Ir complexes coordinating with acetyl acetone as disclosed in E.P. Pat. No. 1434286 and a blue phosphorescent Ir complex with an emission wavelength exceeding 500 nm and quantum efficiency exceeding 5% as disclosed in U.S. Pat. No. 2002024293. Orange phosphorescent Ir complexes, however, have yet to be effectively provided, regarding compounds such as $Bt_2Ir(acac)$ with an emission wavelength of about 560 nm provided by Thompson as disclosed in J. Am. Chem. Soc. 2001, 123, 4304~4312 and an orange phosphorescent Ir complex with emission wavelength of about 570 nm as disclosed in G.P. Pat. No. 2003040250.

SUMMARY

The invention provides an organometallic complex having formula (I):

(I)

n = 0~5 wherein A1 is a substituted or non-substituted aromatic heterocyclic group, A2 is a substituted or non-substituted aryl group, A3 is an acetylacetone group or picolinic acid group, and X is selected from the group consisting of fluorine atom, trifluoromethyl, alkoxy, thioalkyl, and amino.

The invention also provides an organic electroluminescent device comprising a pair of electrodes and an organic electroluminescent layer installed therebetween, utilizing the disclosed organometallic complex.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION

The invention provides an organometallic complex having formula (I):

(I)

n = 0~5

In formula (I), A1 is a substituted or non-substituted aromatic heterocyclic group such as thiophenyl, benzothiophenyl, furanyl, or pyridinyl, preferably thiophenyl or benzothiophenyl. A2 is a substituted or non-substituted aryl group such as benzene, benzothiophene, or naphthalene. A3 is an acetylacetone group or picolinic acid group. X may comprise fluorine atom, trifluoromethyl, alkoxy, thioalkyl, or amino groups.

The specific organometallic complexes provided by the invention comprise wherein A3 is an acetylacetone group or picolinic acid group.

The compound of formula (I) is prepared as follows. First, a coordination compound such as phenyl thienopyridine, naphthalenyl thienopyridine, or phenyl benzothienopyridine is prepared by general synthesis. Next, the coordination compound, a metal halide, solvent, and deionized water are added to a flask with thermal reflux for about 45~50 hours. The metal halide may be $IrCl_3 \cdot H_2O$, and the solvent may be 2-ethoxy ethanol. After cooling to room temperature, and filtration, collected solids are washed with a small quantity of solvent such as water or methanol. An organometallic dimer is prepared after drying. Next, the organometallic dimmer and a salt, such as $Na_2CO_3$, a bidentate compound, and solvent, such as 2-ethoxy ethanol, are mixed in a flask and stirred with heating for about 20~25 hours. The bidentate compound comprises acetyl acetone or picolinic acid. After cooling to room temperature, and filtration, collected solids are washed with a small quantity of solvent such as water or methanol, an organometallic complex (formula (I)) containing two coordination groups and a bidentate group is prepared.

Due to strong spin-orbital coupling, electrons of a $d^6$ Ir complex may span multiple energy levels to form a triplet excited state by Metal to Ligand Charge Transfer (MLCT) and mixed $\pi$-$\pi$* coordination orbits, resulting in increased phosphorescent luminescent efficiency with low drive voltage requirement. Emission wavelength of the phosphorescent complex appears in an orange or yellow light region of about 530~600 nm. Electroluminescent devices comprising the Ir complex can more easily meet the NTSC standard.

The invention also provides an organic electroluminescent device comprising a pair of electrodes and an organic electroluminescent layer installed therebetween, utilizing the disclosed organometallic complex as formula (I).

The organic electroluminescent layer comprises an emitting layer comprising the disclosed organometallic complex used as a red luminescent dopant. Hosts of the emitting layer comprise CBP, TCTA, CzTT, TPBI, TAZ, BAlq, MCP, UGHI, UGH2, or UGH3. The organic electroluminescent layer further comprises a hole transport layer, a hole blocking layer, an electron transport layer, or a buffer layer. The hole transport layer comprises HTM2, TPD, NPB, PPD, TBPB, spiro-TAD, spiro-NPB, TPTE2, TPTE1, NTPA, or DNPD. The hole blocking layer comprises BPhen BCP, BAlq, CF-X, TAZ, or CF-Y. The electron transport layer comprises t-Bu-PBD, Alq$_3$, BeBq, TAZ, Almq3, BAlq, or TPBI. The buffer layer may comprise LiF or Li$_2$O. The foregoing abbreviations represent the following structures.

-continued

-continued

CF-Y

HTM2

TPD

NPB

PPD

-continued

TBPB spiro-TAD spiro-NPB

TPTE2

-continued

TPTE1

NTPA

DNPD

-continued

A method of fabricating an organic electroluminescent device is further provided. An anode is provided on a substrate and a hole transport layer is evaporated on the anode to a thickness of about 400~600 Å. A Ir complex (dopant) and host are then co-evaporated on the hole transport layer to form an emitting layer at a thickness of about 150~250 Å, with dopant/host volume ratio about 5~10%. Next, a hole blocking layer is evaporated on the emitting layer to a thickness of about 100~200 Å. An electron transport layer is evaporated on the hole blocking layer to a thickness of about 100~200 Å. A buffer layer is evaporated on the electron transport layer to a thickness of about 3~10 Å. Finally, a cathode is evaporated on the buffer layer to a thickness of about 1000~1400 Å.

The organic electroluminescent device has a drive voltage of about 4.66~5.55V, brightness of about 220~400 cd/m$^2$ or 20~45 cd/A, luminescent efficiency of about 12.4~26.1 lm/W, a CIEx value of about 0.47~0.50, a CIEy value of about 0.49~0.51, and a luminescent wavelength of about 560~580 nm.

EXAMPLES

Example 1

Preparation of Compound 1

(1) 1 g phenyl-thiophen-3-yl-methanone (compound 1a), 1.03 g 2,2-dimethoxy-ethylamine, and 15 ml toluene were added to a 50 ml round-bottomed flask and stirred at 110° C. for 12 hours. After returning to room temperature, 2,2-dimethoxy-ethylamine was removed by low-pressure distillation. Remaining solution was then purified by a column (ethyl acetate:n-hexane=1:4) to finally form 1.12 g yellow compound 1b with yield of 83%. The reaction according to step (1) was (2) 2.75 g compound 1b and 10 g PPA were added to a 50 ml round-bottomed flask and stirred at 120° C. for 6 hours. After returning to room temperature, 200 ml water was added. A proper quantity of KOH was then added to neutralize the solution to a basic condition. Organo-layer was extracted by adding 120 ml ethyl acetate. Remaining water in the organo-layer was then removed by adding 2 g MgSO$_4$. After the organo-layer condensed, 1.79 g white compound 1c solids were prepared with yield of 85%. The reaction according to step (2) was (3) 0.725 g compound 1c, 0.57 g IrCl$_3$*H$_2$O, 15 ml 2-ethoxy ethanol, and 5 ml water were added to a flask with reflux at 110° C. for 48 hours. After returning to room temperature, solvent was distilled by a low-pressured distillation. 0.743 g yellow compound 1d powders were prepared after drying with yield of 81%. The reaction according to step (3) was (4) 1.46 g compound 1d, 1.12 g acetic acetone, 0.59 g Na₂CO₃, and 20 ml 2-ethoxy ethanol were added to a flask and stirred at 120° C. for 24 hours. After returning to room temperature, solvent was distilled by a low-pressured distillation. 1.6 g yellow compound 1 powders were prepared after drying with yield of 68%. The reaction according to step (3) was Example 2

Preparation of Compound 2

(1) 1 g phenyl-thiophen-2-yl-methanone (compound 2a), 1.03 g 2,2-dimethoxy-ethylamine, and 15 ml toluene were added to a 50 ml round-bottomed flask and stirred at 110° C. for 12 hours. After returning to room temperature, 2,2-dimethoxy-ethylamine was removed by low-pressure distillation. Remaining solution was then purified by a column (ethyl acetate:n-hexane=1:4) to finally form 1.09 g yellow compound 2b with yield of 81%. The reaction according to step (1) was -continued (2) 2.5 g compound 2b and 9 g PPA were added to a 50 ml round-bottomed flask and stirred at 120° C. for 6 hours. After returning to room temperature, 200 ml water was added. A proper quantity of KOH was then added to neutralize the solution to a basic condition. Organo-layer was extracted by adding 120 ml ethyl acetate. Remaining water in the organo-layer was then removed by adding 2 g MgSO₄. After the organo-layer condensed, 1.53 g white compound 2c solids were prepared with yield of 80%. The reaction according to step (2) was

(3) 0.8 g compound 2c, 0.62 g IrCl₃, 15 ml 2-ethoxy ethanol, and 5 ml water were added to a flask with reflux at 110° C. for 48 hours. After returning to room temperature, solvent was distilled by a low-pressured distillation. 0.79 g yellow compound 2d powders were prepared after drying with yield of 78%. The reaction according to step (3) was -continued (4) 1.5 g compound 2d, 1.21 g acetic acetone, 0.6 g $Na_2CO_3$, and 20 ml 2-ethoxy ethanol were added to a flask and stirred at 120° C. for 24 hours. After returning to room temperature, solvent was distilled by a low-pressured distillation. 1.43 g yellow compound 2 powders were prepared after drying with yield of 61%. The reaction according to step (3) was Example 3

Fabrication of Organic Electroluminescent Device

Figure 1:
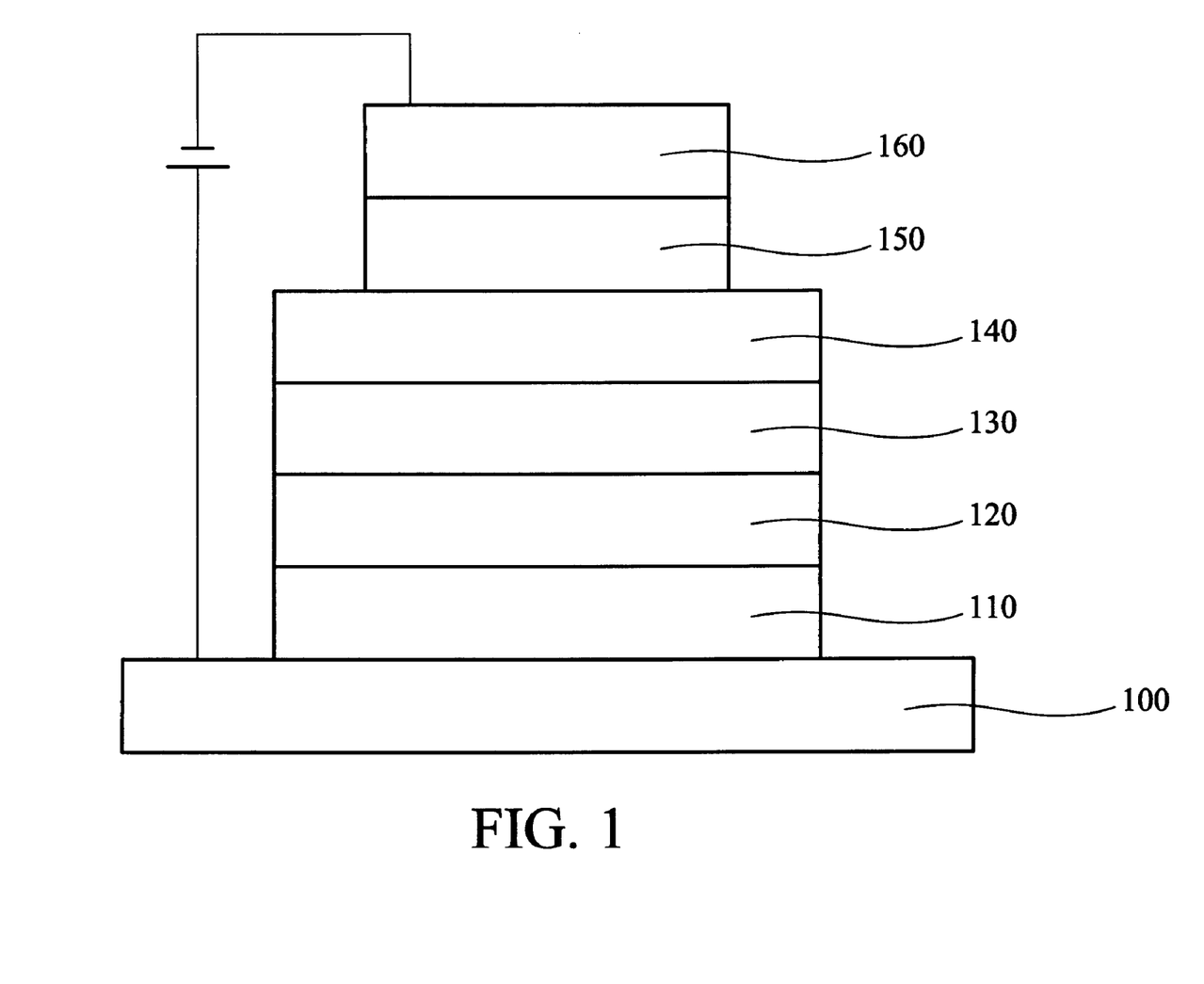
FIG. 1 is a cross section of an organic electroluminescent device of the invention.

Referring to FIG. 1, a method of fabricating an organic electroluminescent device is disclosed according to the following example, in which an ITO anode 100 was provided on a substrate and washed with cleaning agent and deionized water. After drying, NPB was evaporated on the ITO anode 100 to form a hole transport layer 110 at a thickness of 500 Å. Ir complex (compound 1, dopant) and CBP (host) were then co-evaporated on the hole transport layer 110 to form an emitting layer 120 at a thickness of 200 Å. The dopant/host volume ratio thereof was 6%. Next, BCP was evaporated on the emitting layer 120 to form a hole blocking layer 130 at a thickness of 150 Å. Next, $Alq_3$ was evaporated on the hole blocking layer 130 to form an electron transport layer 140 at a thickness of 200 Å. Next, LiF was evaporated on the electron transport layer 140 to form a buffer layer 150 at a thickness of 5 Å. Finally, Al was evaporated on the buffer layer 150 to form a cathode 160 at a thickness of 1200 Å.

The invention also provides three devices utilizing various dopants and concentrations in emitting layers, for example, doping with 6% compound 2, 9% compound 1, and 9% compound 2, respectively, in emitting layers.

Referring to Table 1, various drive voltages, brightness, CIE values, and wavelengths of the foregoing devices were compared.

TABLE 1

| dopant | Compound 1 (6%) | Compound 1 (9%) | Compound 2 (6%) | Compound 2 (9%) |
| --- | --- | --- | --- | --- |
| Drive voltage (Volts) | 5.21 | 4.66 | 5.55 | 5.46 |
| Brightness ($cd/m^2$) | 399 | 390 | 222 | 288 |
| Brightness (cd/A) | 40.3 | 38.7 | 21.9 | 28.7 |
| Luminescent efficiency (lm/W) | 24.3 | 26.1 | 12.4 | 16.5 |
| CIE (x, y) values | (0.48, 0.50) | (0.49, 0.50) | (0.49, 0.50) | (0.49, 0.50) |
| Wavelength (nm) | 560 | 560 | 564 | 564 |

The data in Table 1, such as drive voltages, brightness, and luminescent efficiency, were measured at current density of merely 1 mA/cm. Clearly, the organic electroluminescent devices of the invention provide low drive voltage requirements and high luminescent efficiency.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organometallic complex selected from the group consisting of wherein A3 is an acetylacetone group or a picolinic acid group.

2. The organometallic complex as claimed in claim 1, wherein the organometallic complex is a luminescent material.

3. The organometallic complex as claimed in claim 1, wherein the organometallic complex is an orange phosphorescent dopant.

4. The organometallic complex as claimed in claim 1, wherein A3 is the acetylacetone group.

5. The organometallic complex as claimed in claim 1, wherein A3 is the picolinic acid group.

6. An organic electroluminescent device, comprising:
 a pair of electrodes; and
 an organic electroluminescent layer installed between the electrodes, comprising an organometallic complex as claimed in claim 1.

7. The organic electroluminescent device as claimed in claim 6, wherein the organic electroluminescent layer comprises an emitting layer comprising the organometallic complex.

8. The organic electroluminescent device as claimed in claim 7, wherein the organometallic complex is an orange luminescent dopant.

9. The organic electroluminescent device as claimed in claim 6, wherein the organic electroluminescent layer comprises a hole transport layer, a hole blocking layer, an electron transport layer, or a buffer layer.

10. The organic electroluminescent device as claimed in claim 6, wherein the organic electroluminescent device has a drive voltage of about 4.66-5.55V.

11. The organic electroluminescent device as claimed in claim 6, wherein the organic electroluminescent device has a brightness of about 220-400 $cd/m^2$.

12. The organic electroluminescent device as claimed in claim 6, wherein the organic electroluminescent device has a brightness of about 20-45 cd/A.

13. The organic electroluminescent device as claimed in claim 6, wherein the organic electroluminescent device has a luminescent efficiency of about 12.4-26.1 lm/W.

14. The organic electroluminescent device as claimed in claim 6, wherein the organic electroluminescent device has a CIEx value of about 0.47-0.50 and a CIEy value of about 0.49-0.51.

15. The organic electroluminescent device as claimed in claim 6, wherein the organic electroluminescent device has a luminescent wavelength of about 560-580 nm.

* * * * *